United States Patent [19]

Drent

[11] Patent Number: 4,824,817
[45] Date of Patent: Apr. 25, 1989

[54] CATALYST FOR THE CARBONYLATION OF CONJUGATED DIENES

[75] Inventor: Eit Drent, CM Amsterdam, Netherlands

[73] Assignee: Shell Oil Company, Houston, Tex.

[21] Appl. No.: 124,128

[22] Filed: Nov. 23, 1987

[30] Foreign Application Priority Data

Dec. 5, 1986 [NL] Netherlands .................. 8603101

[51] Int. Cl.$^4$ .................. B01J 31/04; B01J 31/02; B01J 31/12
[52] U.S. Cl. .................. 502/154; 502/162; 502/167; 502/170; 560/207; 562/522
[58] Field of Search .............. 502/154, 162, 167, 170

[56] References Cited

U.S. PATENT DOCUMENTS

| | | | |
|---|---|---|---|
| 3,887,595 | 6/1975 | Nozaki | 260/410.6 |
| 4,172,087 | 10/1979 | Knifton | 260/410.6 |
| 4,243,829 | 1/1981 | Pittman et al. | 502/162 X |
| 4,292,437 | 9/1981 | Squire | 502/162 X |
| 4,471,067 | 9/1984 | Foley | 502/162 |
| 4,501,822 | 2/1985 | Foley | 502/162 |
| 4,582,817 | 4/1986 | Hanes | 502/170 X |

FOREIGN PATENT DOCUMENTS

| | | | |
|---|---|---|---|
| 198521 | 10/1986 | European Pat. Off. | |
| 2450802 | 11/1980 | France | 502/170 |
| 2058074 | 4/1981 | United Kingdom . | |

Primary Examiner—Patrick P. Garvin
Attorney, Agent, or Firm—Y Grace Tsang

[57] ABSTRACT

A catalyst system for the selective carbonylation of conjugated dienes in the presence of a hydroxyl-group-containing compound in the liquid phase comprising a combination of:
(a) palladium or a compound of;
(b) an organic phosphorus, antimony or arsenic derivative according to the formula:
wherein $R_1$ represents an aryl group substituted with at least one electron-attracting group and $R_2$ and $R_3$ each represent individually an aryl group or an aryl group substituted with at least one electron-attracting group and $R_2$ and $R_3$ each represent individually an aryl group or an aryl group substituted with at least one electron-attracting group and wherein Q represents phosphine, antimony or arsenic; and
(c) an acid with a pka from about 2.5 to about 4.0, said acid being a condensed aromatic carboxylic acid or a benzoic acid substituted with at least one electron attracting group selected from the group consisting of (1) halogen, (2) hydroxy, and (3) methoxy.

11 Claims, No Drawings

CATALYST FOR THE CARBONYLATION OF CONJUGATED DIENES

FIELD OF THE INVENTION

This invention relates to a process for the carbonylation of conjugated dienes and, in particular, to the preparation of 3-pentenoic acid and derivatives thereof from 1,3-butadiene and to similar conversions of homologous dienes. The invention also includes a novel palladium-containing catalyst which can be utilized for the carbonylation reaction.

BACKGROUND OF THE INVENTION

Processes for carbonylating olefinically unsaturated hydrocarbons are known from U.S. Pat. Nos. 3,887,595 issued June 3, 1975 and 4,172,087 issued Oct. 23, 1979 inter alia.

In U.S. Pat. No. 3,887,595 a process is described for the carbonylation of olefinically unsaturated hydrocarbons of 2 to 30 carbon atoms, free of acetylenic unsaturation and conjugated olefinic unsaturation with carbon monoxide and with at least one hydroxyl compound, selected from a group consisting of water, alkanol having 1 to 20 carbon atoms, carboxylic acid having 2 to 20 carbon atoms and mixtures thereof, in the presence of a catalyst, with formation of predominantly straight-chain products, using as the catalyst a composition essentially consisting of:

(a) a zero valent noble metal phosphine complex wherein the metal consists of palladium or platinum and is surrounded by 1 to 4 ligands, consisting of phosphines comprising three optionally substituted hydrocarbon moieties of 1 to 20 carbon atoms, free of aliphatic carbon-carbon unsaturation and selected from the group formed by alkyl, unsubstituted phenyl, monosubstituted alkyl and, (b) from about 10 mole to about 150 mole of the phosphine per mole of the metal phosphine complex concerned.

From U.S. Pat. No. 4,172,087 a process is known for the simultaneous preparation of two groups of unsaturated carboxylic acids and ester thereof from aliphatically conjugated diene substrates containing from 4 to 8 carbon atoms wherein:

(a) every two moles of the aliphatically conjugated diene concerned are mixed with a three-component mixture consisting of (i) at least a catalytic quantity of a palladium catalyst consisting of either one or more palladium halide salts in combination with one or more monodentate tertiary phosphorus containing donor ligands, or one or more palladium halide free salts in combination with one or more multidentate, tertiary phosphorus containing donor ligands;

(ii) at least one molar equivalent of a hydroxyl group containing co-reactant, selected from the group consisting of water or an aliphatic alkanol containing 1 to 12 carbon atoms; and (iii) an N-heterocyclic amine base in order to form a reaction mixture;

(b) the reaction mixture is pressurized with sufficient carbon monoxide to satisfy the stoichiometry of the carbonylation reaction, (c) the pressurized reaction mixture is heated up to temperatures of 30° C. to 150° C. until substantial formation of the desired aliphatic carboxylic acid derivatives has been achieved, and (d) the unsaturated carboxylic acid derivatives concerned that occur therein are isolated.

Preferably, 1,3-butadiene is used as a starting material, while pyridine, alkylated pyridines, quinoline, lutidine, picoline, isoquinoline, alkylated quinolines and isoquinolines and acridine or N,N-dimethylaniline, N,N-diethylaniline, N,N-diethyltoluidine and N,N-dibutyltoluidine and N,N-dimethylformamide and N-methyl-2-pyrrolidone can be used a N-heterocyclic amine base.

It will be clear that the processes described hereinbefore do not relate precisely to the selective conversion of conjugated unsaturated compounds nor, in particular, to the selective preparation of 3-pentenoic acid and derivatives thereof, which is becoming an increasingly important base material for organic syntheses (for example, for the preparation of adipic acid and derivatives thereof), have been diverted away from the methods described hereinbefore.

Most of the known butadiene conversion methods are, moveover, characterized by the use of relatively large concentrations of hydrochloric acid or other hydrohalogenic acids and otherwise rigorous reaction conditions, whereby supplementary, mostly cost-increasing measures have been necessary on account of safety and apparatus (corrosion).

An improved process has now been surprisingly found for the selective conversion of conjugated dienes in the liquid phase and particularly for the selective preparation of 3-pentenoic acid or derivatives thereof by the conversion of 1,3-butadiene and analogous conversions of isoprene, 2-methylbutadiene, 1,3-hexadiene and analogous conversions of isoprene, 2-methylbutadiene, 1,3-hexadiene, 2,4-hexadiene, 2,4-heptadiene and higher homologues, with a generally increased conversion rate, in the presence of a characteristic catalyst system.

SUMMARY OF THE INVENTION

The invention therefore provides a process for the selective carbonylation of conjugated dienes, such as 1,3-butadiene, isoprene, 2,4-hexadiene, 2,4-heptadiene and higher homologues in the presence of a hydroxyl group containing compound such as water, alcohol, phenol or carboxylic acid, in the liquid phase and in the presence of a catalyst system to be prepared by a combination of:

(a) palladium or a compound thereof,
(b) an organic phosphorus, antimony or arsenic derivative according to the general formula:

wherein $R_1$ represents an aryl group substituted with one or more electron-attracting groups and $R_2$ and $R_3$ each represents individually an aryl group or an aryl group substituted with one or more electron-attracting groups and wherein Q represents phosphorus, antimony or arsenic, and (c) a substituted benzoic acid with a pKa<4 and more particularly a benzoic acid containing a phenyl group substituted with one or more electron-attracting substituents and/or which forms part of a large condensed aromatic ring system.

The invention also includes the catalyst systems, as mentioned hereinbefore, useful for the selective carbonylation of conjugated dienes.

DETAILED DESCRIPTION OF THE INVENTION

The selectivity towards, for example, 3-pentenoic acid or derivatives thereof, expressed as a percentage, is defined as $$\frac{a}{b} \times 100$$

wherein "a" is, for example, the quantity of 1,3-butadiene that is coverted into 3-pentenoic acid or derivatives thereof, and "b" the total converted quantity of 1,3-butadiene.

It will be clear that the very high selectivity that has been found for the conversion of, for example, 1,3-butadiene into 3-pentenoic acid and derivatives thereof is achieved at the cost of the 3,8-nonadienic acid or derivatives thereof additionally and simultaneously formed in the known processes.

A particularly preferred group of said compounds comprises the group according to a general formula I, wherein Q is phosphorus and wherein the aryl groups contain up to a maximum of 18 carbon atoms in the ring, such as anthryl, naphthyl and phenyl, preferably phenyl.

Greater preference is given to the phosphines according to formula I wherein $R_1$, $R_2$ and $R_3$ each represent individually a phenyl group substituted with one or more electron-attracting groups. Examples of such electron-attracting groups are chlorine, bromine, fluorine, monochloromethyl, trichloromethyl, trifluoromethyl, nitroand m-methoxy groups.

Examples of phosphines suitable for use in accordance with the present invention are:
tri(m-chlorophenyl) phosphine,
phenyl di(m-chlorophenyl) phosphine,
diphenyl (m-chlorophenyl) phosphine,
phenyl di(p-chlorophenyl) phosphine,
diphenyl (p-chlorophenyl) phosphine,
tri(m-trifluoromethylphenyl) phosphine,
phenyl di(trifluoromethylphenyl) phosphine,
diphenyl (m-trifluoromethylphenyl) phosphine,
phenyl di(trichloromethylphenyl) phosphine,
diphenyl (trichloromethylphenyl) phosphine,
diphenyl (m-methoxyphenyl)phosphine,
phenyl di(m-methoxyphenyl) phosphine,
phenyl (dichloromethylphenyl) phosphine,
diphenyl (chloromethylphenyl) phosphine,
diphenyl (nitrophenyl) phosphine,
phenyl di(nitrphenyl) phosphine and
tri(p-chlorophenyl)phosphine.

Very good conversion results can be achieved with halogen, monohalogen methyl, dihalogen methyl, trihalogen methyl groups as substituents, particularly with chloro- or trifluoromethyl groups.

The most highly preferred phosphines are tri(m-chlorophenyl) phosphine, tri(p-chlorophenyl) phosphine and tri(m-trifluoromethylphenyl) phosphine.

The substituted benzoic acids used in accordance with the invention have a pKa value < 4.0 an preferably between 2.5 and 4, measured at 18° C. in aqueous solution. Examples of such acids are benzoic acids having the phenyl group substituted with one or more electron-attracting groups such as halogen and, in particular, chlorine, such as o-chlorobenzoic acid, m-chlorobenzoic acid, p-chlorobenzoic acid, o-hydroxybenzoic acid, o-methoxybenzoic acid, o-bromobenzoic acid, m-bromobenzoic acid, 2,6-dichlorobenzoic acid and 9-anthracenecarboxylic acid.

According to a further embodiment of the process according to the invention, apart from the monodentate phosphines referred to hereinbefore bidentate phosphines can also be used with attractive results. In particular, apart from one or more of the monodentate phosphines referred to hereinbefore, bidentate phosphines can be used wherein the phenyl groups have been optionally substituted with electron-attracting groups a such as:
1,2-ethanediyl bis di(chlorophenyl) phosphine,
1,4-butanediyl bis di(chlorophenyl) phosphine,
1,2-ethenediyl bis di(trifluoromethylphenyl) phosphine,
1,2-ethanediyl bis di(trifluoromethylphenyl) phosphine,
1,2-phenylene bis di(chlorophenyl) phosphine,
1,2-tetrafluorocyclobutene diyl bis di(chlorophenyl) phosphine
1,2-tetrafluoroclobutene diyl bis di(trifluoromethylphenyl) phosphine,
1,2-hexafluorocyclopentene diyl bis di(chlorophenyl) phosphine,
1,2-octafluorocyclohexene diyl bis di(chlorophenyl) phosphine,
bis (o-diphenylphosphinophenyl) chlorophenyl phosphine,
1,2-ethanediyl bis di(phenyl) phosphine,
1,4-butanediyl bis di(phenyl) phosphine,
1,2-ethenediyl bis di(phenyl) phosphine,
1,2-ethanediyl bis phenyl(chlorophenyl) phosphine,
1,2-phenylene bis diphenyl phosphine,
1,2-tetrafluorocyclobutene diyl bis diphenyl phosphine,
1,2-hexafluorocyclopentene diyl bis diphenyl phosphine,
1,2-octafluorocyclohexene diyl bis diphenyl phosphine,
1,2-hexafluorocyclopentene diyl bis diphenyl(chlorophenyl) phosphine and
1,2-hexafluorocyclopentene diyl bis diphenyl(trifluoromethylphenyl) phosphine.

Both homogeneous and heterogeneous palladium catalyst components can be used for the process according to the invention. Homogeneous catalyst components are preferred. Suitable homogeneous catalyst components are formed by salts of palladium with, for example, nitric acid, sulphuric acid or alkanecarboxylic acids containing not more than 12 carbon atoms per molecule. Salts of hydrohalogens are not preferred on account of the corrosive effect caused by halide ions. A catalyst component preferred for use is palladium acetate. Palladium complexes may also be used, such as palladiumacetyl acetonate, bis-tri-o-tolylphosphinepalladium acetate or bistriphenylphosphinepalladium acetate.

The quantity of palladium is not critical. In the event that a bivalent palladium compound is used, preference is given to the use of quantities in the range between $10^{-5}$ and $10^{-1}$ gram atom palladium per mole conjugated diene, preferably butadiene.

The molar ratio of the organic phosphorus, arsenic or antimony compound to palladium is not critical and can vary between wide limits. Preferably, more than 2 moles of the preferably used phosphine is used per gram atom palladium in order to achieve a very high selectivity in conjunction with a good conversion rate. Very high selectivities and very high conversion rates are achieved if more than 2 and less than 20 moles of the organic phosphine is used per gram atom palladium.

The number of equivalents used of the organic phosphine per protonic acid equivalent is not critical either and can vary between wide limits. Quantities of 0.1 to 10 substituted benzoic acid equivalents per organic phosphine equivalent used are suitable.

In general, it is desirable to use a separate solvent in said conversion process. Any inert solvent may be used for this purpose. This may, for example, be selected from sulfones, for example diisopropyl sulfone; aromatic hydrocarbons such as benzene, toluene, xylenes; esters such as methylacetate and butyrolactone; ketones such as acetone or methyl isobutyl ketone; and ethers such as anisole, 2,5,8-trioxanone (also referred to as diglyme), diphenyl ether, diisopropyl ether and tetrahydrofuran. Preferably, an ether such as diphenyl ether is used.

The process according to the invention allows the use of relatively mild reaction conditions. Temperatures in the range from 50° C. to 200° C., particularly from 50° C. to 155° C., are suitable.

The quantity of, for example, the 1,3-butadiene can vary over a wide range. The carbon monoxide pressure will generally be lower than that according to the processes known hitherto. Pressures of 5 to 60 bar are preferred.

The molar ratio of the alcohol, phenol, water or carboxylic acid to the conjugated diene and, in particular, butadiene can vary between wide limits and generally lies in the range from 0.1:1 to 10:1. According to one of the preferred embodiments of the process according to the invention, an alcohol can be used as hydroxyl-containing reactant. The alcohol can be aliphatic, cycloaliphatic or aromatic and can, if necessary, carry one or more inert substituents. A suitable alcohol can contain up to 20 carbon atoms. One or more hydroxyl groups can be present, in which case various products can be formed, depending on the molar ratio of the reactants used. For example, a polyvalent alcohol such as ethylene glycol, glycerol, butane diol, 2,2-dihydroxymethyl-1-butanol can be allowed to react with a suitable quantity of butadiene to form a monoester or a polyvalent ester. The choice of alcohol will therefore depend solely on the product desired. Alkanols such as methanol, ethanol, propanol or 2,2-dihydroxymethyl-1-butanol and alcohols containing ether bridges such as triethylene glycol all yield valuable products.

According to another embodiment of the process according to the invention, a wide variety of carboxylic acids can be used as reactant. For example, the carboxylic acids can be aliphatic, cycloaliphatic or aromatic and may optionally carry inert substituents. Suitable carboxylic acids contain not more than 25 carbon atoms. The carboxylic acids used as reactant are preferably alkanecarboxylic acids or alkenecarboxylic acids. Examples of suitable carboxylic acids are formic acid, acetic acid, propionic acid, n-butyric acid, isobutyric acid, pivalic acid, n-valeric acid, n-caproic acid, caprylic acid, capric acid, lauric acid, myristic acid, palmitic acid, stearic acid, phthalic acid, terephthalic acid. Examples of alkenecarboxylic acids are acrylic acid, propiolic acid, methacrylic acid, crotonic acid, isocrotonic acid, olic acid, maleic acid, fumaric acid, citraconic acid and mesaconic acid.

The process according to the invention may, in principle also be applied with polyvalent carboxylic acids whereby, depending on the reaction conditions selected, including the molar ratio of the reactants used, various products can be obtained as required. If an alkanecarboxylic acid is converted according to the process of the invention with 1,3-butadiene, a symmetrical or composite anhydride can be formed.

It will be clear that another aspect of the invention in question is formed by the catalyst systems referred to hereinbefore that are to be used for the selective conversion of conjugated dienes, as such or in the form of a solution in one of the solvents referred to hereinbefore suitable for that purpose.

The invention is expounded with the aid of the following Examples without the scope thereof being limited to them. More than 90% of the pentenoate formed in the course thereof consists of 3(cis and trans)pentenoate.

The ranges and limitations provided in the instant specification and claims are those which are believed to particularly point out and distinctly claim the instant invention. It is, however, understood that other ranges and limitations that perform substantially the same function in substantially the same manner to obtain the same or substantially the same result are intended to be within the scope of the instant invention as defined by the instant specification and claims.

EXAMPLE 1

A 250 ml magnetically stirred HASTELLOY® autoclave was successively filled with 15 ml ethanol, 40 ml diphenyl ether, 1 mmole palladium acetate, 6 mmole tri(meta-chlorophenyl) phosphine and 20 mmole 2,6-dichlorobenzoic acid. The autoclave was vacuum-evacuated, whereupon butadiene (8 ml) and carbon monoxide were added to an initial pressure of 30 bar. The autoclave was closed and heated to 135° C. After a reaction time of 3 hours the contents of the autoclave were analysed by means of gas-liquid chromatography. The selectivity of butadiene conversion towards pentenoates was found to be 95%, while the pentenoate yield, more than 90% of which consisted of ethyl 3-(cis and trans)pentenoates, was 85% of the butadiene starting quantity. A comparative experiment was performed in a virtually analogous manner as described hereinbefore, but with 2,4,6-trimethylbenzoic acid (20 mmole) as catalyst component instead of 2,6-dichlorobenzoic acid, which after a reaction time of 5 hours resulted in a selectivity of butadiene to pentenoate conversion of 50% (as a result of nonadienoate formation) and a pentenoate yield of 10%, calculated in terms of the butadiene starting quantity, which clearly indicates the specificity of the protonic acids to be used in accordance with the invention. The same effect transpires from a comparative experiment performed in a virtually analogous manner wherein triphenyl phosphine (6 mmole) was used instead of the tri(meta-chlorophenyl) phosphine as catalyst component, methanol (10 ml) instead of ethanol and 2,6-dichlorobenzoic acid (20 mmole) as promoter acid. After a reaction time of 5 hours, this resulted in a selective conversion of butadiene into pentenoates of <50% and a pentenoate yield, calculated in terms of the butadiene starting quantity, of 10%.

EXAMPLE 2

In a virtually analogous manner as described in Example 1, an experiment was performed with a catalyst system composed of palladium acetate (1 mmole), tri(-para-chlorophenyl) phosphine (8 mmole), 2,6-dichlorobenzoic acid (7.5 mmole) and 15 ml ethanol, while the reaction temperature was 125° C. and the reaction time 2.5 hours. The initial carbon monoxide pressure in this experiment was 60 bar and the butadiene starting quantity 17 ml. The selectivity of butadiene to pentenoate conversion was 95%, while the pentenoate yield was 48% in terms of the butadiene starting quantity.

EXAMPLE 3

In a virtually analogous manner as described in Example 1, an experiment was performed with a catalyst system composed of palladium acetate (1 mmole), tri(-meta-chlorophenyl) phosphine (6 mmole) and 9-anthracenecarboxylic acid (20 mmole). The reaction temperature was 135° C. and the reaction time 5 hours. The selectivity of butadiene to pentenoate conversion was 90% and the pentenoate yield, calculated in terms of the starting butadiene quantity, was 70%. For comparison, a virtually analogous experiment was performed as in Example 1, except that no acid was used in the catalyst system. After a reaction time of 5 hours at 155° C., selectivity in respect of pentenoates was found to be 90%, but the pentenoate yield, calculated in terms of the starting butadiene quantity, was merely 25%.

EXAMPLE 4

In a virtually analogous manner as described in Example 1, an experiment was performed with a catalyst system composed of palladium acetate (1 mmole), tri(-meta-chlorophenyl) phosphine (4 mmole), 1,4-butanediyl-bis-diphenyl-phosphine (4 mmole), 2,6-dichlorobenzoic acid (20 mmole) and 10 ml methanol. Initial carbon monoxide pressure was 60 bar, reaction time 5 hours and reaction temperature 155° C. The selectivity of butadiene conversion towards pentenoates was 95% and the pentenoate yield in terms of the starting butadiene quantity was 85%.

EXAMPLE 5

In a virtually analogous manner as described in Example 1, an experiment was performed with a catalyst system composed of palladium acetate (1 mmole), tri(-para-fluorophenyl) phosphine (6 mmole) and 2,6-dichlorobenzoic acid. Initial carbon monoxide pressure was 60 bar, reaction time 5 hours and reaction temperature 135° C. Selectivity of butadiene conversion towards pentenoates was 95% and the pentenoate yield in terms of the starting butadiene quantity was 87%.

EXAMPLE 6

In a virtually analogous manner as described in Example 1, an experiment was performed with a catalyst system composed of palladium acetate (1 mmole), tri(-para-chlorophenyl) phosphine (6 mmole), 9-anthracenecarboxylic acid (20 mmole) and 15 ml acetic acid. Initial carbon monoxide pressure was 60 bar, reaction temperature 115° C. and reaction time 5 hours. Selectivity of butadiene conversion towards pentenoic acid and derivatives thereof was 90% and the yield of pentenoic acid and derivatives thereof, calculated in terms of the starting butadiene quantity, was 60%. In this experiment, acetic anhydride was formed apart from pentencic acids and derivatives thereof.

EXAMPLE 7

In a virtually analogous manner as described in Example 1, an experiment was performed with a catalyst system consisting of 0.4 mmole palladium acetate, 6 mmole tri(meta-chlorophenyl) phosphine, 4 mmole 2,6-dichlorobenzoic acid and 10 g phenol. Initial carbon monoxide pressure was 40 bar, reaction time 5 hours and temperature reaction 115° C. Selectivity of butadiene conversion towards phenyl pentenoate was 80% and the pentenoate yield, calculated in terms of the butadiene starting quantity, was 60%.

What is claimed is:

1. A catalyst system for the selective carbonylation of conjugated dienes in the presence of a hydroxyl group containing compound in the liquid phase comprises a combination of:
   (a) palladium or a compound thereof;
   (b) an organic phosphorus, antimony or arsenic derivative according to the formula:

wherein $R_1$ represents an aryl group substituted with at least one electron-attracting group and $R_2$ and $R_3$ each represent individually an aryl group or an aryl group substituted with at least one electron-attracting group and wherein Q represents phosphine, antimony or arsenic; and
   (c) an acid with a pka from about 2.5 to about 4.0, said acid is a condensed aromatic carboxylic acid or a benzoic acid substituted by at least one electron-attracting group selected from the group consisting of (1) halogen, (2) hydroxy, and (3) methoxy.

2. The catalyst systems as claimed in claim 1, characterized in that the acid is selected from the group consisting of o-chlorobenzoic acid, m-chlorobenzoic acid, p-chlorobenzoic acid, 2,6-dichlorobenzoic acid, o-hydroxybenzoic acid, o-methoxybenzoic acid, o-bromobenzoic acid and 9-anthracenecarboxylic acid.

3. The catalyst systems as claimed in claim 1, characterized in that said acid is 2,6-dichlorobenzoic acid or 9-anthracenecarboxylic acid.

4. The catalyst systems as claimed in claim 1, characterized in that (b) is a phosphine wherein said aryl groups are phenyl groups substituted with halogen, or monohalogen methyl, dihalogen methyl or trihalogen methyl groups.

5. The catalyst systems as claimed in claim 4, characterized said phosphine is selected from the group consisting of tri(m-chlorophenyl) phosphine, tri(p-chlorophenyl) phosphine, tri(m-fluoromethyl) phosphine or tri(m-fluoromethylphenyl) phosphine.

6. The catalyst systems as claimed in claim 1, characterized in that it further comprises bidentate phosphine(s).

7. The catalyst system as claimed in claim 1, characterized in that said palladium compound is palladium acetate.

8. The catalyst system as claimed in claim 7, characterized in that the concentration of said phosphine is from about 2 to about 20 mole phosphine per gram atom palladium.

9. The catalyst systems as claimed in claim 8, characterized in that the concentration of said acid is from about 0.1 to about 10 equivalents of the acid per organic phosphine equivalent.

10. The catalyst systems as claimed in claim 1, characterized in that it further comprises an inert solvent.

11. A catalyst system for the carbonylation of butadiene in the presence of a hydroxyl group containing compound in the liquid phase which comprises a combination of
(a) from about $10^{-5}$ to $10^{-1}$ gram atom palladium acetate per mole of butadiene;
(b) about 2-20 moles of an organic phosphine per gram atom of (a), the phosphine is selected from the group consisting of tri(m-chloro phenyl)phosphine, tri(p-chlorophenyl) phosphine, tri(m-trifluoromethyl phenyl) phosphine and tri(p-fluorophenyl) phosphine; and
(c) from about 0.1 1 to about 10 equivalent 2,6-dichlorobenzoic acid or 9-anthracenecarboxylic acid per equivalent of (b).

* * * * *